US006335398B1

(12) United States Patent
Amiya et al.

(10) Patent No.: US 6,335,398 B1
(45) Date of Patent: *Jan. 1, 2002

(54) SUPER ABSORBENT POLYMER COMPOSITION

(75) Inventors: Takayuki Amiya; Seiichi Miyanaga; Yoko Hanada, all of Wakayama (JP)

(73) Assignee: Kao Corporation, Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/809,013

(22) PCT Filed: Jun. 16, 1995

(86) PCT No.: PCT/JP95/01200

§ 371 Date: Mar. 7, 1997

§ 102(e) Date: Mar. 7, 1997

(87) PCT Pub. No.: WO96/07437

PCT Pub. Date: Mar. 14, 1996

(30) Foreign Application Priority Data

Sep. 9, 1994 (JP) ............................................. 6-216102
Nov. 14, 1994 (JP) ............................................. 6-279396

(51) Int. Cl.$^7$ ............................................. C08G 63/48
(52) U.S. Cl. .................. 525/54.3; 525/54.31; 525/288; 525/296; 525/329.5; 525/329.8; 525/329.9; 525/340; 525/360; 525/364; 525/374; 525/377; 525/378; 525/379; 525/380; 525/386; 525/418
(58) Field of Search ................................ 524/145, 54.3, 524/54.31, 296, 288, 329.5, 329.8, 329.9, 340, 360, 364, 374, 378, 379, 377, 380, 386, 418

(56) References Cited

U.S. PATENT DOCUMENTS

| 4,024,073 A | * | 5/1977 | Shimizu et al. ............. 252/316 |
| 4,048,410 A | * | 9/1977 | Taylor et al. ................. 526/22 |
| 4,583,980 A | * | 4/1986 | Schneider et al. .......... 604/359 |
| 5,086,841 A | * | 2/1992 | Reid et al. .................. 166/295 |
| 5,098,608 A | * | 3/1992 | Miyazawa et al. .......... 252/546 |
| 5,288,500 A | * | 2/1994 | Ibsen ......................... 424/489 |
| 5,486,312 A | * | 1/1996 | Sandiford et al. ........ 252/315.1 |
| 5,509,913 A | * | 4/1996 | Yeo .......................... 525/330.2 |
| 5,617,920 A | * | 4/1997 | Dovan et al. ................ 166/295 |

FOREIGN PATENT DOCUMENTS

| EP | 0372981 A2 | 6/1990 |
| JP | 2255804 | 10/1990 |
| JP | 3179008 | 8/1991 |

OTHER PUBLICATIONS

Taqui Khan et al., J. American Chemical Society, 89:16, 4176–4185 (Aug. 1967).
Buettner, Free Rad. Res. Comms., vol. 1, No. 6, 349–353 (1986).
Herp et al., Carbohydrate Research, vol. 4, 63–71, (1967).

* cited by examiner

Primary Examiner—Judy M. Reddick
(74) Attorney, Agent, or Firm—Birch, Stewart, Kolasch & Birch, LLP

(57) ABSTRACT

A super absorbent polymer composition comprising a chelating compound (A) which has a site capable of forming a chelate with a copper ion and whose copper salt has a solubility in physiological saline at 25° C. of 0.01% by weight or less and a super absorbent polymer (B), wherein the chelating compound (A) is present in an amount of from 0.0001 to 30 parts by weight per 100 parts by weight of said super absorbent polymer (B).

6 Claims, No Drawings

US 6,335,398 B1

SUPER ABSORBENT POLYMER COMPOSITION

TECHNICAL FIELD

The present invention relates to a super absorbent polymer composition in which a super absorbent polymer has improved stability. More particularly, it relates to a super absorbent polymer composition in which a super absorbent polymer is protected against decomposition and/or deterioration even in a water-containing state, i.e., containing an aqueous liquid or a body fluid such as urine, blood and sweat.

BACKGROUND ART

Super absorbent polymers have been used widely as an absorbent material in disposable diapers for babies, adults and persons suffering from incontinence or sanitary napkins in the field of sanitation; water-retaining materials in the field of agriculture and horticulture; and coagulants for sludge, materials for preventing dew drop condensation or water stopping materials in the field of construction. It is known that water-soluble high-molecular weight compounds constituting such super absorbent polymers undergo reduction in molecular weight and deterioration with time in the presence of radical generating species, such as hydrogen peroxide or L-ascorbic acid or salts thereof.

Body fluids such as urine, blood and sweat contain L-ascorbic acid or salts thereof. Therefore, it has been a great problem that a super absorbent polymer used in a disposable diaper or a sanitary napkin having absorbed therein such a body fluid undergoes decomposition and deterioration with time by the action of the radical species generated from L-ascorbic acid or salts thereof and therefore reduces its capacity of retaining the body fluid.

The decomposition of a super absorbent polymer due to radical generating species is pronounced in its water-containing state in an air atmosphere, especially in the presence of an aqueous solution containing transition metal ions, such as iron and copper, capable of having an oxidation number of 2 or more.

This is because a trace amount of a transition metal ion, such as iron and copper, acts as a catalyst to markedly accelerate the decomposition reaction (radical generating reaction) of hydrogen peroxide, or L-ascorbic acid or salts thereof, as described in J. Am. Chem. Soc., 89, No. 16, 4176 (1967) and Free Radical Research Communications, 1, No. 6, 349 (1986).

These transition metal ions are known, like radical generating species such as hydrogen peroxide or L-ascorbic acid or salts thereof, to cause depolymerization of water-soluble polymers with time (see, e.g., Carbohydrate Research, 4, 63 (1967)).

Means that have been widely employed for suppressing decomposition and deterioration of super absorbent polymers include (1) sealing of a super absorbent polymer under reduced pressure or in a nitrogen atmosphere to avoid contact with air (especially with oxygen), (2) use of highly purified water and reagents to inhibit incorporation of metal ions into a super absorbent polymer, (3) addition of an antioxidant or a reducing agent to a super absorbent polymer, (4) addition of a protein or an enzyme to a super absorbent polymer, and (5) addition of a metal chelating agent, such as citric acid, (poly)phosphoric acid or salts thereof, or ethylenediaminetetraacetic acid (EDTA) or salts thereof, to a super absorbent polymer (JP-A-63-146964 corresponding to EP-A-257951).

In many cases, however, means (1) and (2) are impossible to carry out for some end uses of a super absorbent polymer. Means (3), (4) and (5) including addition of a known additive suppress decomposition and deterioration of a super absorbent polymer, but the effect exerted is not always sufficient. Cases are often met with in which the additive must be added in a large quantity or an additive having a very strong action must be used. Under such a situation, it is likely that the inherent physical properties or performances of super absorbent polymers should be impaired seriously. Additionally, where the system containing a super absorbent polymer is used in direct contact with a human body or a plant or an animal, adverse influences on the living system give rise to a problem.

In fact, various methods for suppressing decomposition and deterioration of super absorbent polymers have been proposed to date. For example, Japanese Patent Application Laid-Open 63-272349 (corresponding to EP-A-268459, U.S. Pat. No. 4,959,060), Japanese Patent Publication 5-34383 (corresponding to EP-A-249391, U.S. Pat. No. 4,972,019), and Japanese Patent Application Laid-Open 2-255804 (corresponding to EP-A-372981) and 3-179008 disclose a method of using additives such as a sulfur-containing reducing agent, an oxygen-containing reducing inorganic salt, a water-soluble chain transfer agent. Nevertheless, these additives have a disadvantage of giving off an offensive odor or being an irritant and/or an allergen and need sufficient care for safety when actually used under such conditions that the additive may contact with a human body. Thus, an additive having higher safety has been keenly demanded.

DISCLOSURE OF THE INVENTION

Accordingly, an object of the present invention is to provide a super absorbent polymer composition in which the super absorbent polymer can exist stably without undergoing decomposition and deterioration even in the presence of an aqueous solution or water containing radical generating species, such as hydrogen peroxide or L-ascorbic acid or salts thereof, and which has high safety for a living system.

The present inventors have conducted extensive investigations to solve the above-mentioned problem. As a result, they have found that a super absorbent polymer in a water-absorbing state can be stabilized by inhibiting a decomposition reaction (radical generating reaction) of radical generating species, such as hydrogen peroxide or L-ascorbic acid or salts thereof and that this can be achieved by completely sequestering a transition metal ion acting as a catalyst for the radical generating reaction by converting the transition metal ion into a water-insoluble chelate.

The present invention has been reached based on the above finding. That is, the above object of the present invention is accomplished by a super absorbent polymer composition comprising a chelating compound (A) which has a site capable of forming a chelate with a copper ion and whose copper salt has a solubility in physiological saline at 25° C. of 0.01% by weight or less (excluding β-diketone derivatives) and a super absorbent polymer (B), wherein said chelating compound (A) is present in an amount of from 0.0001 to 30 parts by weight per 100 parts by weight of said super absorbent polymer (B).

The super absorbent polymer composition of the present invention is effectively used, though dependent on the kind of the super absorbent polymer used, in combination with cosmetics or food additives containing radical generating species, such as ascorbic acid. The super absorbent polymer composition of the present invention is particularly suitable as an absorbent material of sanitary articles.

DETAILED DESCRIPTION OF THE INVENTION

The super absorbent polymer composition of the present invention will be described below in detail.

The super absorbent polymer (B) which can be used in the present invention is not particularly limited. Examples of usable super absorbent polymer (B) include partially crosslinked polymers having a carboxyl group or salts thereof, such as a crosslinked polyacrylic acid salt, a crosslinked poly(vinyl alcohol/acrylic acid salt) copolymer, a (crosslinked) starch-acrylic acid salt graft copolymer, and a crosslinked polyvinyl alcohol-poly(maleic anhydride salt) graft copolymer; and partially crosslinked polysaccharides, such as a crosslinked carboxymethyl cellulose salt. From the viewpoint of water absorption capacity, it is preferable to use a crosslinked polyacrylic acid salt or a (crosslinked) starch-acrylic acid salt graft copolymer, with a crosslinked polyacrylic acid salt being especially preferred.

These super absorbent polymers (B) may be used either individually or in combination of two or more thereof.

The salt in the super absorbent polymers includes, for example, an alkali metal salt, an alkaline earth metal salt, and an ammonium salt. The degree of neutralization of the super absorbent polymers is from 0.01 to 100%, preferably from 1 to 99%, still preferably from 40 to 95%, based on the number of moles of the acid groups in the super absorbent polymer.

The chelating compound (A) which can be used in the present invention has a site capable of forming a chelate with a copper ion, and the copper salt thereof has a solubility in physiological saline at 25° C. of 0.01% by weight or less. The term "site capable of forming a chelate with a copper ion" as used herein means a site capable of forming a coordination bond with a metal ion in a compound which is generally considered to act as a ligand in the field of complex chemistry. The term "solubility" as used herein means a concentration (wt %) obtained by dividing [a maximum amount (weight) of a copper salt of the chelating agent which dissolves in physiological saline at 25° C. to make a clear solution after stirred for 30 minutes] by [the weight of the solution].

The chelating compound (A) is safer than conventional additives that have been used as a stabilizer for super absorbent polymers and is yet equal or superior to those additives in stabilizing effect for super absorbent polymers.

The chelating compound (A) is preferably used in an amount of from 0.0001 to 30 parts by weight, still preferably from 0.001 to 10 parts by weight, and particularly from 0.01 to 5 parts by weight, per 100 parts by weight of the super absorbent polymer. Addition of less than 0.0001 part of chelating compound (A) produces no effect. Addition of more than 30 parts by weight shows no further improvement, rather tending to impair the physical properties of the super absorbent polymer. Therefore, the amount of chelating compound (A) to be used preferably falls within the above-specified range.

It is particularly preferable that chelating compound (A) is capable of forming such a chelate with $Cu^{2+}$ ion at 25° C., expressed in a common logarithm value (hereinafter sometimes referred to as pKCu), is about 3 or greater. If the pKCu is less than about 3, the chelating compound sometimes has insufficient performance as a stabilizer for a super absorbent polymer.

No limitation is imposed on the type of the chelating compound (A) to be used in the present invention as far as the above-mentioned physical properties are satisfied. Preferred examples of the chelating compounds (A) include the following compounds (1) and (2):

(1) Compounds which comprise a hydrophobic moiety having a saturated or an unsaturated hydrocarbon group having 6 or more carbon atoms and a hydrophilic moiety having at least one group selected from the group consisting of a carboxyl group, a sulfo group, a hydroxyl group and a phospho group; and (2) Tropolone derivatives.

In the present invention, one or more compounds selected from any of the compounds (1) and (2) can be used. Compounds selected respectively from at least 2 groups (1) and (2) may be used in combination.

It is also preferable that the chelating compounds in combination have a pKCu of about 3 or higher.

The chelating compound (A) belonging to the group (1) comprises a hydrophobic moiety having a saturated or an unsaturated hydrocarbon group having 6 or more carbon atoms (preferably 6 to 30, more preferably 12 to 22) and a hydrophilic moiety having at least one group selected from the group consisting of a carboxyl group, a sulfo group, a hydroxyl group and a phospho group. The saturated hydrocarbon group includes a straight-chain or branched alkyl group, or a cycloalkyl group. The unsaturated hydrocarbon group includes a straight-chain or branched alkenyl group, or a phenyl group. Examples of chelating compounds (A) having such groups are polycarboxylic acid derivatives, hydroxycarboxylic acid derivatives, iminodiacetic acid derivatives, organic acid amide derivatives, N-acyl amino acid derivatives, phosphate ester derivatives phosphonic acid derivatives and polyphosphonic acid derivatives as well as their alkali metal salts and alkaline earth metal salts.

The polycarboxylic acid derivatives include alkylmalonic acids and alkenylmalonic acids as well as salts thereof. The hydroxycarboxylic acid derivatives include monoalkyl citrates and monoalkenyl citrates as well as salts thereof. The iminodiacetic acid derivatives include N-alkyl-N'-carboxymethylaspartic acids, N-alkenyl-N'-carboxymethylaspartic acids and salts thereof. The organic acid amide derivatives include citric acid monoalkylamides, citric acid monoalkenylamides and salts thereof. The N-acyl amino acid derivatives include an N-acyl glutamic acid, an N-acyl aspartic acid and salts thereof. The phosphate ester derivatives include monoalkyl phosphates, monoalkenyl phosphates and salts thereof. The phosphonic acid derivatives include alkylphosphonic acid, alkenylphosphonic acid and salts thereof, and phenylphosphonic acid and salts thereof. The polyphosphonic acid derivatives include alkylenebis(nitrilodimethylene)tetraphosphonic acids and salts thereof.

Preferred among them are citric acid monoalkylamides, citric acid monoalkenylamides and salts thereof; monoalkyl citrates, monoalkenyl citrates and salts thereof; alkylmalonic acids, alkenylmalonic acids and salts thereof; N-alkyl-N'-carboxymethylaspartic acids, N-alkenyl-N'-carboxymethylaspartic acids and salts thereof; N-acyl glutamic acids and salts thereof; and monoalkyl phosphates, monoalkenyl phosphates and salts thereof. In particular, citric acid derivatives including citric acid monoalkylamides, citric acid monoalkenylamides and salts thereof, and monoalkyl citrates, monoalkenyl citrates and salts thereof are still preferred for their high effects on stabilizing super absorbent polymers. N-acyl amino acid derivatives are also preferred for the same reason.

The above-mentioned citric acid monoalkylamides, citric acid monoalkenylamides and salts thereof preferably include those represented by formula (I):

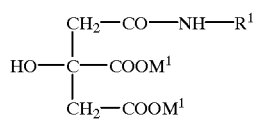

(I)

wherein $R^1$ represents an alkyl or alkenyl group having 6 to 30 carbon atoms; and $M^{1}$'s, which may be the same or different, each represents an alkali metal ion, an ammonium ion or a hydrogen.

The citric acid monoalkylamides, citric acid monoalkenylamides and salts thereof can be synthesized by known methods. For example, they are obtained by subjecting an amine and citric acid to complete dehydrating condensation to form an imine, which is then hydrolyzed, followed by neutralization. A proper choice of the number of carbon atoms of $R^1$ in formula (I) affords a citric acid monoalkylamide, a citric acid monoalkenylamide or salts thereof that meets the purpose. If the number of carbon atoms of $R^1$ exceeds 30, the resulting compound has considerably reduced water solubility. If it is less than 6, the performance of the resulting compound as a stabilizer for super absorbent polymers is reduced. The number of carbon atoms of $R^1$ preferably ranges from 12 to 22.

The monoalkyl citrates, monoalkenyl citrates and salts thereof preferably include those represented by formula (II):

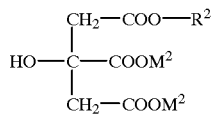

(II)

wherein $R^2$ represents an alkyl or alkenyl group having 6 to 30 carbon atoms; and $M^{2}$'s, which may be the same or different, each represents an alkali metal ion, an ammonium ion or a hydrogen.

These monoalkyl citrates, monoalkenyl citrates and salts thereof can be synthesized by known methods. For example, they are obtained through dehydrating condensation of an alcohol and citric acid. A proper choice of the number of carbon atoms of $R^2$ in formula (II) affords a monoalkyl citrate, a monoalkenyl citrate or salts thereof that meets the purpose. If the number of carbon atoms of $R^2$ exceeds 30, the resulting compound has considerably reduced water solubility. If it is less than 6, the performance of the resulting compound as a stabilizer for super absorbent polymers is reduced. The number of carbon atoms of $R^2$ preferably ranges from 12 to 22.

The alkylmalonic acids, alkenylmalonic acids and salts thereof preferably include those represented by formula (III):

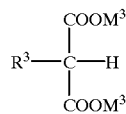

(III)

wherein $R^3$ represents an alkyl or alkenyl group having 6 to 30 carbon atoms; and $M^{3}$'s, which may be the same or different, each represents an alkali metal ion, an ammonium ion or a hydrogen.

These alkylmalonic acids, alkenylmalonic acids and salts thereof can be synthesized by known methods. For example, they are obtained by adding an α-olefin to methyl malonate or ethyl malonate to obtain a methyl alkylmalonate or an ethyl alkylmalonate, which is then hydrolyzed, followed by neutralization. A proper choice of the number of carbon atoms of $R^3$ in formula (III) affords an alkylmalonic acid, an alkenylmalonic acid or salts thereof that meets the purpose. If the number of carbon atoms of $R^3$ exceeds 30, the resulting compound has considerably reduced water solubility. If it is less than 6, the performance of the resulting compound as a stabilizer for super absorbent polymers is reduced. The number of carbon atoms of $R^3$ preferably ranges from 12 to 22.

The above-mentioned N-alkyl-N'-carboxymethylaspartic acid, N-alkenyl-N'-carboxymethylaspartic acid and salts thereof preferably include those represented by formula (IV):

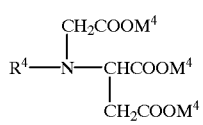

(IV)

wherein $R^4$ represents an alkyl or alkenyl group having 6 to 30 carbon atoms; and $M^{4}$'s, which may be the same or different, each represents an alkali metal ion, an ammonium ion or a hydrogen.

These N-alkyl-N'-carboxymethylaspartic acids, N-alkenyl-N'-carboxymethylaspartic acids and salts thereof can be synthesized by known methods. For example, they are obtained by adding an amine to maleic acid to obtain an alkylaminosuccinic acid, which is then carboxymethylated with carboxymethyl chloride, followed by neutralization. A proper choice of the number of carbon atoms of $R^4$ in formula (IV) affords an N-alkyl-N'-carboxymethylaspartic acid, an N-alkenyl-N'-carboxymethylaspartic acid or salts thereof that meets the purpose. If the number of carbon atoms of $R^4$ exceeds 30, the resulting compound has considerably reduced water solubility. If it is less than 6, the performance of the resulting compound as a stabilizer for super absorbent polymers is reduced. The number of carbon atoms of $R^4$ preferably ranges from 12 to 22.

The monoalkyl phosphates, monoalkenyl phosphates and salts thereof preferably include those represented by formula (V):

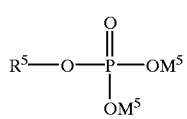

(V)

wherein $R^5$ represents an alkyl or alkenyl group having 6 to 30 carbon atoms; and $M^{5}$'s, which may be the same or different, each represents an alkali metal ion, an ammonium ion or a hydrogen.

The above monoalkyl phosphates, monoalkenyl phosphates and salts thereof can be synthesized by known methods. For example, they are obtained by esterifying an alcohol with phosphorus pentoxide, phosphorus oxychloride or polyphosphoric acid. A proper choice of the number of carbon atoms of $R^5$ in formula (V) affords a monoalkyl phosphate, a monoalkenyl phosphate or salts thereof that meets the purpose. If the number of carbon atoms of $R^5$ exceeds 30, the resulting compound has considerably reduced water solubility. If it is less than 6, the performance of the resulting compound as a stabilizer for super absorbent polymers is reduced. The number of carbon atoms of $R^5$ preferably ranges from 12 to 22.

The above-mentioned N-acyl glutamic acid and the salts thereof are preferably represented by the following formula (VI).

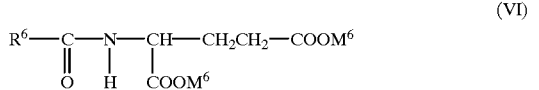

wherein $R^6$—CO— represents acyl group having 6 to 30 carbon atoms, $M^6$'s which may be the same or different, each represents alkali metal ion, an ammonium ion, a triethanol ammonium ion or a hydrogen.

The N-acyl glutamic acid and salts thereof can be synthesized by known method, and it is also commercially available. A proper choice of the number of carbon atoms of $R^6$—CO— in formulation (VI) affords N-acyl glutamic acid or salts thereof which meets the purpose. If the number of the carbon atoms in $R^6$—CO— is less than 6, performance of the super absorbent resin as a stabilizer is reduced. The number of carbon atoms of $R^6$—CO— preferably ranges from 12 to 22.

The N-acyl aspartic acid and salts thereof preferably include those represented by formula (VII).

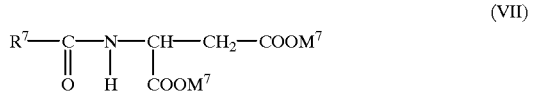

wherein $R^7$—CO— represents acyl group having 6 to 30 carbon atoms, $M^7$'s which may be the same or different, each represents an alkali metal ion, an ammonium ion, a triethanol ammonium ion or a hydrogen.

The N-acyl aspartic acid and salts thereof can be synthesized by known method, and it is also commercially available. A proper choice of the number of carbon atoms of $R^7$—CO— in formula (VII) affords a N-acyl aspartic acid or salts thereof which meets the purpose. If the number of the carbon atoms of $R^7$—CO— exceeds 30, the resulting compound has considerably reduced water solubility. If it is less than 6, the performance of the resulting compound as a stabilizer for super absorbent polymers is reduced. The number of the carbon atoms of $R^7$—CO— preferably ranges from 12 to 22.

The chelating compounds (A) of the above-mentioned compounds (1) are safer and more effective to inhibit decomposition and deterioration of super absorbent polymers than the additives conventionally employed as a stabilizer for super absorbent polymers.

The chelating compounds (A) of the compounds (1) may be used either individually or in combination of two or more thereof.

The tropolone derivatives of the above-mentioned compounds (2) are compounds capable of forming a chelate with a copper ion, and the copper salts of the tropolone derivatives have a solubility in physiological saline at 25° C. of 0.01% by weight or less. Such tropolone derivatives are naturally-occurring substances found in certain kinds of trees. They have high safety having no serious influences on a human body, an animal or a plant even in contact in a high concentration. Use of the tropolone derivative for stabilization of super absorbent polymers, i.e., prevention of decomposition and deterioration of super absorbent polymers has been unknown. In particular, use of a super absorbent polymer composition containing the tropolone derivative as an absorbent material of sanitary articles, such as absorbing articles, has been unknown. They are safer and more effective to inhibit decomposition and deterioration of super absorbent polymers than the additives conventionally employed as a stabilizer for super absorbent polymers.

While specific but not-limiting examples of the tropolone derivatives are tropolone, β-thujaplicin, γ-thujaplicin, β-dolabrin and methyl 6-isopropyltropolone-4-carboxylate, as well as sodium or potassium salt thereof. Preferred of them are β-thujaplicin and γ-thujaplicin. Inter alia, β-thujaplicin is preferred for its safety to a living body as having been used as a perfume for hair tonics, toothpaste, perfume preparations, external preparations, bath agents, shampoos and rinses.

The tropolone derivatives may be synthetics or semi-synthetics. It is also possible to use natural hiba oil or hinoki oil containing these tropolone derivatives either as such or after purification.

These tropolone derivatives may be used either individually or in combination of two or more thereof.

The super absorbent polymer composition according to the present invention may contain water in addition to the components (A) and (B) just like a water-containing polymer or a water-containing gel. The composition may be formulated into an aqueous composition by dispersing the super absorbent polymer in water or mixing the polymer with water like an aqueous dispersion or emulsion. If desired, the composition of the present invention may contain various additives, such as a water-soluble organic solvent, a surface active agent, salts, a stabilizer, an antioxidant and/or an antiseptic.

While the super absorbent polymer of the present invention may have any form as far as it contains the components (A) and (B), it is preferably used in the form of an aqueous dispersion or emulsion containing components (A) and (B), a solid mixture of components (A) and (B), and a solid of component (B) impregnated with component (A). A form in which component (B) contains therein component (A) is particularly preferred.

The super absorbent polymer composition of the present invention can be prepared, for example, by the following methods:

(1) A method in which solid components (A) and solid component (B) are ground and mixed;

(2) A method in which component (B) is impregnated with an aqueous solution or dispersion of component (A), followed by drying;

(3) A method in which component (B) is impregnated with a solution of component (A) in a hydrophilic organic solvent, followed by drying;

(4) A method in which an aqueous solution or organic solvent solution of component (A) is applied to component (B), followed by drying;

(5) A method in which component (A) is heat-melted, applied to component (B), and cooled; and (6) A method in which components (A) and (B) are mixed in water and used as such.

As stated previously, the super absorbent polymer composition of the present invention is particularly useful as a water absorbing material in sanitary articles, such as absorbent articles, e.g., disposable diapers and sanitary napkins.

These absorbent articles comprise a water-permeable topsheet, a water-impermeable back sheet and an absorbent member interposed between the topsheet and the back sheet. The absorbent member to be used comprises fluff pulp, i.e., comminuted wood pulp, in combination with the super absorbent polymer composition of the present invention. The super absorbent polymer composition may be mixed with fluff pulp or be provided in the form of a layer in a specific part of the absorbent member, i.e., in any of the upper layer, the middle layer and the lower layer. In another embodiment, a mixture of a thermoplastic resin, fluff pulp and the super absorbent polymer composition of the present invention may be heat-treated to provide an integral absorbent member. Since a body fluid such as urine contains substances such as L-ascorbic acid or a salts thereof as previously mentioned, a super absorbent polymer in an absorbent article having absorbed therein a body fluid undergoes deterioration caused by these substances. According to the present invention, such deterioration of a super absorbent polymer can be suppressed by using the super absorbent polymer composition of the present invention as an absorbent material of an absorbent article. Absorbent articles using the super absorbent polymer composition of the present invention hardly cause a back-flow of the absorbed body fluid which is ascribed to deterioration of the super absorbent polymer. As a result, absorbent articles such as disposal diapers and sanitary napkins can be used for a long time, for example, in the nighttime with freedom from care.

The present invention will be illustrated in greater detail with reference to Examples and Comparative Examples, but it should be understood that the present invention is not deemed to be limited thereto. All the percents are given by weight unless otherwise indicated.

EXAMPLES

The reagents used in Examples and Comparative Examples are commercially available reagents. Na salt of N-acyl glutamic acid is Amisoft HS-21, a product of Ajinomoto K.K.; β-Thujaplicin and γ-thujaplicin are products of Takasago Corporation. The citric acid monoalkylamide Na salt, monoalkyl citrate Na salt, monooleyl citrate, alkylmalonic acid, N-alkyl-N'-carboxymethylaspartic acid, monoalkyl phosphate, monooleyl phosphate and N-acyl aspartic acid K salt were synthesized by conventional methods.

The chelating compounds used in Examples and Comparative Examples are shown in Table 1 together with the solubility of their copper salts and their pKCu values.

The pKCu was obtained by the following procedures. A Cu ion electrode method was used (Orion pH/ion analyzer; Cu ion electrode). A 0.1M triethanolamine-HCl (pH 8) buffer solution was used.

First of all, standard copper ion buffer solutions [400, 320, 240, 160 or 80 ppm (reduced to $Cu^{2+}$)] were prepared using $CuCl_2 \cdot 2H_2O$, and a calibration curve was prepared using a copper ion electrode.

Then, a sample weighing 0.1 g was dissolved in 100 ml of a buffer solution in a measuring flask. To the sample solution was added dropwise a 0.05M $CuCl_2 \cdot 2H_2O$ buffer solution (pH 8) from a burette in 0.6 ml portions, and the potential of the Cu ion electrode was measured. The titration was conducted until the potential exceeded the level corresponding to 400 ppm (reduced to $Cu^{2+}$). Blank measurements were also carried out. A free Cu ion concentration was calculated from the potential, and the calculated value was corrected for the change in amount of the liquid of the measurement system due to the titration. Assuming that addition of an equimolar amount of Cu to a sample produces a 1:1 (by mole) complex, pKCu can be obtained from formula 1:

$$M+L \leftrightarrow ML$$

Stability Constant $K_{ML}=[ML]/([M][L])$

[ML]: Concentration of metal/chelating agent complex

[M]: Concentration of free metal ion

[L]: Concentration of free chelating agent $[M]_T$: [ML]+[M]

$[L]_T$: [ML]+[L]

When $[M]_T=[L]_T$,

[M]=[L]

$[ML]=[L]_T-[L]=[L]_T-[M]$ $K_{ML}=([L]_T-[M])/[M]^2$ $pKCu=\log(K_{ML})=\log\{([L]_T-[M])/[M]^2\}$ 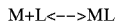 (1)

TABLE 1

|  | Number of Carbon Atoms in Alkyl, Alkenyl or Acyl Group | Solubility of Cu Salt (25° C.) (wt %) | pKCu (25° C.) |
|---|---|---|---|
| β-Thujaplicin | — | <0.0001 | 7.9 |
| γ-Thujaplicin | — | <0.0001 | 7.9 |
| Citric Acid Monoalkylamide 2 Na Salt | 18 16 | 0.001 0.001 | 6.3 6.5 |
| Monoalkyl Citrate Na Salt | 18 | 0.001 | 6.6 |
| Monooleyl Citrate | 18 | 0.001 | 6.4 |
| Alkylmalonic Acid | 16 | 0.001 | 5.1 |
| N-alkyl-N'-Carboxy-methylaspartic Acid | 18 | 0.001 | 4.4 |
| N-acyl Glutamic Acid 2 Na Salt | 18 | <0.0001 | 6.7 |
| N-acyl Aspartic Acid K Salt | 16 | 0.001 | 8.6 |
| Monoalkyl Phosphate | 12 | <0.0001 | 3.2 |
| Monooleyl Phosphate | 18 | <0.0001 | 3.3 |
| EDTA | — | >10 | 18.79 |
| Sodium Tripolyphosphate | — | 1 | 6.8 |
| Trisodium Citrate | — | >10 | 5.2 |

The tests and evaluation in Examples and Comparative Examples were conducted according to the following methods.

1) Water Absorption:

About 1 g of a super absorbent polymer composition was dispersed in a large excess of physiological saline, allowed to be swollen sufficiently, and collected by filtration through a 80 mesh metal net. The swollen sample was weighed, and the wet weight (W) was divided by the dry weight, i.e., the initial weight ($W_0$) to obtain a water absorption.

Water Absorption (g/g)=$W/W_0$

2) Rate of Water Absorption:

Expressed in terms of the amount (ml) of physiological saline absorbed by 1 g of a super absorbent polymer for 3 minutes.

3) Stability:

A super absorbent polymer weighing 1 g was swollen with 45 g of physiological saline containing L-ascorbic acid at a varied concentration. The swollen polymer was put in a screw tube, and the screw tube was placed in a thermostat set at 40° C. After 3 hours, the state of the gel was observed. In Examples 6 to 12 and Comparative Examples 5 to 7, the L-ascorbic acid-containing physiological saline further contained 0.000004% (based on the physiological saline) of $Cu^{2+}$ for accelerated testing.

The stability was rated in 4 grades shown below.

E: The swollen particles retained their shape with neither fluidity nor stringiness.

G: The swollen particles retained their shape, while somewhat showing fluidity and stringiness.

F: The swollen particles showed fluidity and stringiness and had vague shape but were not dissolved.

P: The swollen particles were partly dissolved to liquid, with the majority thereof having no shape.

Example 1

One hundred grams of a super absorbent polymer (Poise SA-20, a product of by Kao Corp.) were put in a double-arm kneader, and 100 g of an ethanol solution containing β-thujaplicin in a concentration of 10%, 1%, 0.1%, 0.01%, 0.001% and 0.0001% was added respectively thereto while stirring. The mixture was thoroughly mixed by stirring followed by drying under reduced pressure.

The water absorption, rate of water absorption and stability of the resulting super absorbent polymer composition were evaluated. The results obtained are shown in Table 2.

Example 2

One hundred grams of a super absorbent polymer (Aqualic CAW-4, a product of Nippon Shokubai Co., Ltd.) were put in a double-arm kneader, and 100 g of an aqueous solution containing γ-thujaplicin in a concentration of 10%, 1%, 0.1%, 0.01%, 0.001% and 0.0001% was added respectively thereto by spraying while stirring the polymer. The mixture was mixed by stirring to let the super absorbent polymer absorb the aqueous solution, followed by drying under reduced pressure.

The water absorption, rate of water absorption and stability of the resulting super absorbent polymer composition were evaluated. The results obtained are shown in Table 2.

Example 3

One hundred grams of a super absorbent polymer (Poise SA-20, a product of Kao Corp.) were put in a double-arm kneader, and 10 g of an ethanol solution containing a β-thujaplicin sodium salt in a concentration of 10%, 1%, 0.1% and 0.01% was added respectively thereto while stirring. The mixture was thoroughly mixed by stirring followed by drying under reduced pressure.

The water absorption, rate of water absorption and stability of the resulting super absorbent polymer composition were evaluated. The results obtained are shown in Table 2.

Example 4

One hundred grams of a super absorbent polymer (Poise SA-20, a product of Kao Corp.) were put in a double-arm kneader, and 100 g of an aqueous solution containing a citric acid monoalkylamide sodium salt (the number of carbon atoms of the alkyl group: 18) in a concentration of 10%, 1%, 0.1% and 0.01% was added respectively thereto while stirring. The mixture was thoroughly mixed by stirring to let the super absorbent polymer absorb the aqueous solution, followed by drying under reduced pressure.

The water absorption, rate of water absorption and stability of the resulting super absorbent polymer composition were evaluated. The results obtained are shown in Table 2.

Comparative Examples 1 to 3

Super absorbent polymers Poise SA-20 (Comparative Example 1), Aqualic, CA (Comparative Example 2) and Diawet (Comparative Example 3) containing no chelating agent were evaluated in the same manner as in Examples 1 to 4. The results obtained are shown in Table 3.

Comparative Example 4

One hundred grams of a super absorbent polymer (Poise SA-20, a product of Kao Corp.) were put in a double-arm kneader, and 100 g of an aqueous solution containing a trisodium citrate salt in a concentration of 1% and 0.1% was added respectively thereto while stirring. The mixture was thoroughly mixed by stirring to let the super absorbent polymer absorb the aqueous solution, followed by drying under reduced pressure.

The resulting super absorbent polymer compositions were evaluated in the same manner as in Example 1 to 4. The results obtained are shown in Table 3.

TABLE 2

| | Amount of Chelating Agent (wt %*) | Amount of L-Ascorbic Acid (wt %*) | Water Absorption (g/g) | Rate of Water Absorption (ml/g - 3 min) | Stability |
|---|---|---|---|---|---|
| Examples | | | | | |
| 1 | 10 | 5.0 | 55.4 | 13.9 | E |
| | 1 | 2.5 | 53.7 | 13.9 | E |
| | 1 | 0.5 | 53.7 | 13.9 | E |
| | 0.1 | 2.5 | 56.0 | 12.2 | E |
| | 0.1 | 0.5 | 56.0 | 12.2 | E |
| | 0.01 | 0.5 | 54.9 | 12.9 | E |
| | 0.01 | 0.1 | 54.9 | 12.9 | E |
| | 0.001 | 0.5 | 55.5 | 12.5 | G |
| | 0.0001 | 0.1 | 55.4 | 13.9 | G |
| 2 | 10 | 5.0 | 53.5 | 15.8 | E |
| | 1 | 2.5 | 53.6 | 15.2 | E |
| | 0.1 | 2.5 | 54.9 | 12.9 | E |
| | 0.1 | 0.5 | 54.9 | 12.9 | E |
| | 0.01 | 2.5 | 54.2 | 14.2 | E |
| | 0.01 | 0.5 | 54.2 | 14.2 | E |

TABLE 2-continued

|   | Amount of Chelating Agent (wt %*) | Amount of L-Ascorbic Acid (wt %*) | Water Absorption (g/g) | Rate of Water Absorption (ml/g - 3 min) | Stability |
|---|---|---|---|---|---|
|   | 0.001 | 0.5 | 53.8 | 13.5 | G |
|   | 0.001 | 0.1 | 53.8 | 13.5 | G |
|   | 0.0001 | 0.5 | 54.1 | 14.5 | G |
| 3 | 1 | 1.0 | 55.4 | 11.6 | E |
|   | 0.1 | 0.5 | 54.9 | 10.6 | E |
|   | 0.01 | 0.5 | 54.3 | 14.9 | E |
|   | 0.001 | 0.1 | 55.5 | 13.5 | G |
| 4 | 10 | 0.5 | 52.9 | 7.9 | E |
|   | 1 | 0.5 | 53.4 | 10.9 | E |
|   | 0.1 | 0.5 | 54.4 | 11.9 | E |
|   | 0.01 | 0.5 | 54.9 | 12.5 | G |

Note:
*Based on the polymer.

TABLE 3

|   | Amount of Chelating Agent (wt %*) | Amount of L-Ascorbic Acid (wt %*) | Water Absorption (g/g) | Rate of Water Absorption (ml/g - 3 min) | Stability |
|---|---|---|---|---|---|
| Comparative Examples |   |   |   |   |   |
| 1 | 0 | 5.0 | 56.7 | 17.5 | F |
|   | 0 | 2.5 | 56.7 | 17.5 | F |
|   | 0 | 0.5 | 56.7 | 17.5 | F |
| 2 | 0 | 5.0 | 54.0 | 28.7 | P |
|   | 0 | 2.5 | 54.0 | 28.7 | P |
|   | 0 | 0.1 | 54.0 | 28.7 | F |
| 3 | 0 | 0.5 | 70.9 | 26.1 | P |
| 4 | 1.0 | 0.5 | 55.7 | 17.2 | F |
|   | 0.1 | 0.5 | 56.8 | 17.8 | F |

Note:
*Based on the polymer.

Synthesis Example 1
(Super Absorbent Polymers (I) and (II))

In a 2L four-necked round flask equipped with a stirrer, a reflux condenser, a dropping funnel, and a tube for introducing nitrogen gas were charged with 1150 ml of cyclohexane and 9.0 g of ethyl cellulose N-200 (a product of Hercules). Nitrogen gas was blown thereinto to drive out dissolved oxygen, and the mixture was heated up to 75° C.

One hundred fifty grams of acrylic acid in a separate flask were neutralized with 65.8 g of 98% sodium hydroxide dissolved in 200 g of ion-exchanged water while externally cooling the acrylic acid. Then, 0.33 g of potassium persulfate was added and dissolved therein, and the solution was transferred to the above dropping funnel and added dropwise to the four-necked flask over a period of 1 hour. After the dropwise addition, the mixture was kept at 75° C. for 30 minutes to continue the reaction. The super absorbent polymer dispersed in the resulting solution is designated super absorbent polymer (I).

Cyclohexane was removed therefrom by distillation under reduced pressure, and the residual super absorbent polymer was dried under reduced pressure to obtain a powdered super absorbent polymer, which is designated super absorbent polymer (II).

Examples to 5 to 8

One hundred grams (dry weight) of super absorbent polymer (I) were put in a double-arm kneader, and 10 g of a 1% aqueous solution of a citric acid monoalkylamide sodium salt (the number of carbon atoms in the alkyl group: 16) (Example 5), 25 g of a 2% aqueous solution of an N-alkyl-N'-carboxymethylaspartic acid (the number of carbon atoms in the alkyl group: 18) (Example 6), 10 g of a 10% aqueous solution of a monoalkyl phosphate (the number of carbon atoms in the alkyl group: 12) (Example 7) or 5 g of a 5% aqueous solution of a monooleyl phosphate (the number of carbon atoms in the alkenyl group: 18) (Example 8) was added to the super absorbent polymer while stirring. The mixture was thoroughly mixed by stirring to let super absorbent polymer (I) absorb the aqueous solution, followed by drying by heating under reduced pressure to obtain a super absorbent polymer composition.

The water absorption, rate of water absorption and stability of the resulting super absorbent polymer composition were evaluated. The results obtained are shown in Table 4.

Examples 9 to 11

One hundred grams of super absorbent polymer (II) were put in a double-arm kneader, and an aqueous solution of 0.1 g of a monoalkyl citrate sodium salt (the number of carbon atoms in the alkyl group: 18) in 20 g of water (Example 9), a dispersion of 0.5 g of monooleyl citrate (the number of carbon atoms in the alkenyl group: 18) in 50 g of water (Example 10) or a dispersion of 1 g of an alkylmalonic acid (the number of carbon atoms in the alkyl group: 16) in 10 g of water (Example 11) was added to the super absorbent polymer while stirring. The mixture was thoroughly mixed by stirring to let super absorbent polymer (II) absorb the aqueous solution, followed by drying by heating under reduced pressure to obtain a super absorbent polymer composition.

The water absorption, rate of water absorption and stability of the resulting super absorbent polymer composition were evaluated. The results obtained are shown in Table 4.

Example 12

A super absorbent polymer composition was prepared and evaluated in the same manner as in Example 5, except for changing the amount of the 1% aqueous solution of a citric acid monoalkylamide sodium salt (the number of carbon atoms in the alkyl group: 16) to 20 g. The results of the evaluation are shown in Table 4.

Example 13

A super absorbent polymer composition was prepared and evaluated in the same manner as in Example 5, except for changing the amount of the 1% aqueous solution of a citric acid monoalkylamide sodium salt (the number of carbon atoms in the alkyl group: 16) to 100 g. The results of the evaluation are shown in Table 4.

The water absorption, rate of water absorption and stability of the resulting super absorbent polymer composition were evaluated. The results obtained are shown in Table 4.

Comparative Examples 5 and 6

One hundred grams (dry weight) of super absorbent polymer (I) were put in a double-arm kneader, and an aqueous solution of 0.1 g of sodium ethylenediaminetetraacetate in 10 g of water (Comparative Example 5) or an aqueous solution of 0.1 g of sodium tripolyphosphate in 10 g of water (Comparative Example 6) was added to the super absorbent polymer while stirring. The mixture was thoroughly mixed by stirring to let super absorbent polymer (I) absorb the aqueous solution, followed by drying by heating under reduced pressure to obtain a super absorbent polymer composition.

The resulting super absorbent polymer compositions were evaluated in the same manner as in Example 5. The results obtained are shown in Table 4.

Comparative Example 7

Super absorbent polymer (II) containing no chelating agent was evaluated in the same manner as in Example 5. The results obtained are shown in Table 4.

TABLE 4

|  | Amount of Chelating Agent (wt %*) | Amount of L-Ascorbic Acid (wt %*) | Water Absorption (g/g) | Rate of Water Absorption (ml/g - 3 min) | Stability |
| --- | --- | --- | --- | --- | --- |
| Examples |  |  |  |  |  |
| 5 | 0.1 | 0.5 | 62 | 17.8 | E |
| 6 | 0.5 | 0.5 | 60 | 16.3 | E |
| 7 | 0.5 | 0.5 | 60 | 16.3 | E |
| 8 | 0.25 | 0.5 | 59 | 19.2 | E |
| 9 | 0.1 | 0.5 | 61 | 19.5 | E |
| 10 | 0.5 | 0.5 | 59 | 18.3 | E |
| 11 | 1.0 | 0.5 | 60 | 20.8 | G |
| 12 | 0.2 | 0.5 | 60 | 17.2 | E |
| 13 | 1.0 | 0.5 | 59 | 14.5 | E |
| 14 | 1.0 | 0.5 | 60 | 18.6 | E |
| 15 | 0.25 | 0.5 | 61 | 19.7 | G |
| Comparative Examples |  |  |  |  |  |
| 5 | 0.1 | 0.5 | 62 | 22.4 | F |
| 6 | 0.1 | 0.5 | 61 | 23.4 | P |
| 7 | 0 | 0.5 | 61 | 23.1 | P |

Note:
*Based on the polymer.

Examples 14 and 15

Two hundred grams (dry weight) of super absorbent polymer (I) were put in a double-arm kneader, and an aqueous solution of 10 g of 20% aqueous solution of N-acyl glutamic acid 2 Na salt (the number of carbon atoms in the acyl group: 18) (Example 14), or an aqueous solution of 5 g of 10% aqueous solution of N-acyl aspartic acid K salt (the number of carbon atoms of the acyl group: 16) (Example 15) was added to the super absorbent polymer while stirring. The mixture was thoroughly mixed by stirring to let super absorbent polymer (I) absorb the aqueous solution, followed by drying by heating under reduced pressure to obtain a super absorbent polymer composition.

INDUSTRIAL APPLICABILITY

The super absorbent polymer composition according to the present invention exhibits excellent water-absorbing properties, allows the super absorbent polymer to exist stably without being deteriorated and/or decomposed even in the presence of an aqueous solution or water containing radical generating species such as hydrogen peroxide and L-ascorbic acid, and a transition metal ion such as iron and copper, and is of high safety for a living system.

Many other variations and modifications of the invention will be apparent to those skilled in the art without departing from the spirit and scope of the invention. The above-described embodiments are, therefore, intended to be merely exemplary, and all such variations and modifications are intended to be included within the scope of the invention as defined in the appended claims.

What is claimed is:

1. A super absorbent polymer composition comprising
a chelating compound (A) which has a site capable of forming a chelate with a copper ion and has a hydrophobic moiety comprising a saturated hydrocarbon group having 6 or more carbon atoms and including a straight-chain alkyl group, a branched alkyl group or a cycloalkyl group, or an unsaturated hydrocarbon group having 6 or more carbon atoms and including a straight-chain alkenyl group, a branched alkenyl group or a phenyl group, and whose copper salt has a solubility in physiological saline at 25° C. of 0.01% by weight or less, wherein said chelating compound (A) is selected from the group consisting of a citric acid monoalkylamide, a citric acid monoalkenylamide, an alkylmalonic acid, an alkenylmalonic acid, an N-acyl glutamic acid, an N-acyl aspartic acid, an N-alkyl-N'-carboxymethylaspartic acid, an N-alkenyl-N'-carboxymethylaspartic acid, a monoalkenyl phosphate, and alkali metal or alkaline earth metal salts thereof; and
a super absorbent polymer (B), wherein
said chelating compound (A) is present in an amount of from 0.0001 to 30 parts by weight per 100 parts by weight of said super absorbent polymer (B).

2. The composition as claimed in claim 1, wherein the stability constant of said chelating compound (A) with $Cu^{2+}$ ion at 25° C., expressed in a common logarithm value (pKCu), is 3 or greater.

3. The composition as claimed in claim 1 or 2, wherein said composition is for use as a water absorbent material for sanitary articles.

4. The composition as claimed in claim 1, wherein said chelating compound (A) is an N-acyl glutamic acid or an N-acyl aspartic acid, or salts thereof.

5. The composition as claimed in claim 1, wherein said super absorbent polymer is selected from the group consisting of a partially crosslinked polymer having a carboxyl group or a salt thereof and a partially crosslinked polysaccharide.

6. The composition as claimed in claim 1, wherein said chelating compound (A) is a citric acid monoalkylamide or a citric acid monoalkenylamide, or salts thereof.

* * * * *